United States Patent [19]

Chang et al.

[11] Patent Number: 4,826,527
[45] Date of Patent: May 2, 1989

[54] AMINOPHENYLMETHYL ISOXAZOLIDINONES AS PLANT REGULATORS

[75] Inventors: Jun H. Chang, Princeton Junction; Jonathan S. Baum, Pennington, both of N.J.

[73] Assignee: FMC Corporation, Philadelphia, Pa.

[21] Appl. No.: 118,101

[22] Filed: Nov. 6, 1987

[51] Int. Cl.$^4$ .................................................. A01N 43/80
[52] U.S. Cl. ............................................. 71/88; 71/74; 71/76; 71/77; 71/78; 71/65
[58] Field of Search ................................... 71/88, 76

[56] References Cited

U.S. PATENT DOCUMENTS 4,405,357  9/1983  Chang ..................................... 71/88
4,552,585 11/1985  Chang ..................................... 71/88
4,692,182  9/1987  Chang ..................................... 71/88

Primary Examiner—Glennon H. Hollrah
Assistant Examiner—A. A. Owens
Attorney, Agent, or Firm—Robert L. Andersen; H. Robinson Ertelt

[57] ABSTRACT

2-[(4-aminophenyl)methyl]-4,4-dimethyl-3-isoxazolidinone plant regulators are represented by the following structural formula

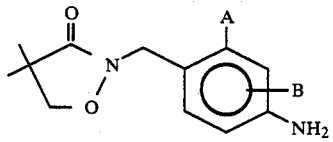

or an agriculturally acceptable salt thereof in which A is hydrogen or halogen, B is hydrogen or halogen, or A and B together form —$C_4H_4$— bridging adjacent carbon atoms and use thereof to modify growth and development of plants are described and exemplified.

1 Claim, No Drawings

AMINOPHENYLMETHYL ISOXAZOLIDINONES AS PLANT REGULATORS

This invention relates to heterocyclic organic chemical compounds which contain an isoxazolidinone nucleus and exhibit plant regulator activity. More specifically, the invention relates to a method and composition for controlling growth and development of plants utilizing certain 2-[(4-aminophenyl)methyl]-4,4-dimethyl-3-isoxazolidinones as the active ingredient.

U.S. Pat. Nos. 4,405,357 and 4,552,585 describe herbicidal 2-[(substituted phenyl)methyl]-4,4-dimethyl-3-isoxazolidinones in which the substituents on the 2-phenylmethyl group include hydrogen, halogen, alkyl, phenyl, haloalkyl, nitro, alkoxy, methylenedioxy, cyano, and amido. U.S. Pat. No. 4,692,182 issued Sept. 8, 1987 describes herbicidal 2-[(substituted phenyl)methyl]-4,4-dimethyl-3-isoxazolidinones in which one substituent on the phenyl ring is a substituted hydrazine group. U.S. Pat. No. 4,552,585 also discloses and claims intermediates for the compounds described above, in which the ring of the 2-phenylmethyl group is amino substituted. None of these patents teach a utility for these amino substituted compounds other than as intermediates.

The present invention relates to chemical compounds which beneficially modify growth and development of plants. Such compounds are hereinafter referred to as plant growth regulators or simply plant regulators. Unlike broad spectrum herbicides, which kill desirable plants as well as weeds, or selective herbicides which minimize effect on desired plants but kill weeds growing adjacent thereto, plant regulators, when applied in the proper manner, exert beneficial effects by selectively modifying the normal growth and development of desirable plants such as agricultural crops.

Beneficial effects from such modification include increasing the yield of fruit, seeds, fiber, or other plant products, increasing the nutritional value of food products derived from the plants, facilitating harvesting of the plant product, or increasing the product's storage life. Plant growth and development modifications leading to such effects include, but are not limited to: root initiation; set, development, ripening and abscission of fruits; modification of plant size and shape; suppression of lodging; control of axillary buds and lateral shoots; metabolism regulation, including senescence and auxin transport inhibition; breaking or enforcing dormancy in seeds, buds, and storage organs; promotion or delay of flowering; defoliation; desiccation; and growth promotion under stress.

Sometimes a compound displays herbicidal and plant growth and development regulation activity depending upon the species of plant, the time of application in the plant growth cycle, the site of application, and the amount of chemical employed, i.e., the application rate. Most of the 2-[(4-aminophenyl)methyl]-4,4-dimethyl-3-isoxazolidinones of this invention can be made to behave as either herbicides or plant regulators depending upon the way they are used.

The 2-[(4-aminophenyl)methyl]-4,4-dimethyl-3-isoxazolidinone plant regulators of the present invention are represented by the following structural formula

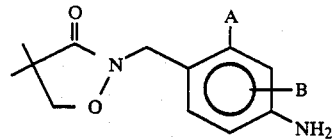

or an agriculturally acceptable salt thereof in which A is hydrogen or halogen, B is hydrogen or halogen, or A and B together form a —C₄H₄— bridging adjacent carbon atoms.

In the aforesaid description and wherever the terms appear hereinafter, unless a contrary intent is clearly expressed, "halo" and "halogen" mean fluorine, chlorine or bromine; the term "lower" modifying an alkyl or other hydrocarbon group implies a straight or branched hydrocarbon chain of 1-6, preferably 1-4, carbon atoms; "halo" coupled with another term means one or more hydrogen atoms has been replaced by halogen; and "cycloalkyl" means a saturated hydrocarbon ring containing 3-8 carbon atoms.

The compounds of this invention may be prepared by the methods disclosed in U.S. Pat. No. 4,552,585 modified by the methods disclosed in Cava et al., Org. Syn. Coll., Vol. V, 944–946, both incorporated herein by reference, and by methods well known to those skilled in the art.

Specific examples of the foregoing compounds, together with compound numbers, and characterizing data are set forth in Table I below. In the characterizing data column, data in parentheses are melting points in °C.

TABLE I

| Cmpd No. | Name | Characterizing Data (°C.) |
| --- | --- | --- |
| 1 | 2-[(4-aminophenyl)methyl]-4,4-dimethyl-3-isoxazolidinone | Solid |
| 2 | 2-[(4-amino-2-chlorophenyl)methyl]-4,4-dimethyl-3-isoxazolidinone | (105–107) |
| 3 | 2-[(4-amino-2-chlorophenyl)methyl]-4,4-dimethyl-3-isoxazolidinone, hydrochloride salt | Solid |
| 4 | 2-[(4-amino-2-bromophenyl)methyl]-4,4-dimethyl-3-isoxazolidinone | (109–111) |
| 5 | 2-[(4-amino-2-fluorophenyl)methyl]-4,4-dimethyl-3-isoxazolidinone | (90–94) |
| 6 | 2-[(4-amino-2-iodophenyl)methyl]-4,4-dimethyl-3-isoxazolidinone | (122–125) |
| 7 | 2-[(4-amino-2,5-dichlorophenyl)methyl]-4,4-dimethyl-3-isoxazolidinone | (117–119) |
| 8 | 2-[(4-amino-2-chloro-5-fluorophenyl)methyl]-4,4-dimethyl-3-isoxazolidinone | (64–66) |
| 9 | 2-[(4-aminonaphth-1-yl)methyl]-4,4-dimethyl-3-isoxazolidinone | (117–120) |

The following examples illustrate the methods for preparation of these compounds.

EXAMPLE 1

SYNTHESIS OF 2-[(4-AMINO-2-CHLOROPHENYL)METHYL]-4,4-DIMETHYL-3-ISOXAZOLIDINONE (Compound 2)

Step A

Synthesis of ethyl (3-chloro-4-methylphenyl)carbamate as an intermediate

Using a method analogous to that disclosed in Example 1, Step A, of U.S. Pat. No. 4,552,585, a solution of 10.0 grams (0.071 mole) of 3-chloro-4-methylaniline in 100 mL of chloroform was stirred, and 16.7 grams (0.212 mole) of pyridine was added. Ethyl chloroformate, 9.2 grams (0.085 mole), was then added dropwise during a 20 minute period. During the addition the reaction mixture temperature was held between 25°–30° C. with external cooling. Upon completion of addition the reaction mixture was stirred at ambient temperature for 16 hours. The reaction mixture was washed into a separatory funnel with 50 mL of chloroform, and the solution was washed with two 100 mL portions of water and 100 mL of aqueous 5% hydrochloric acid. The organic layer was dried with magnesium sulfate and filtered. The filtrate was concentrated under reduced pressure to a waxy solid residue. The residue was recrystallized from hexane to yield 12.2 grams of ethyl (3-chloro-4-methylphenyl)carbamate; m.p. 51°–52° C.

The nmr spectrum was consistent with the proposed structure.

Step B

Synthesis of ethyl (4-bromoethyl-3-chlorophenyl)carbamate as an intermediate

Using a method analogous to that disclosed in Example 1, Step B, of U.S. Pat. No. 4,552,585, a solution of 11.8 grams (0.055 mole) of ethyl (3-chloro-4-methylphenyl)carbamate in 125 mL of carbon tetrachloride was stirred under an argon atmosphere, and 9.8 grams (0.055 mole) of N-bromosuccinimide was added. The reaction mixture was irradiated with a 250 watt brooder lamp, placed at such a distance as to cause a gentle reflux. The reflux was continued for 20 hours. The reaction mixture was cooled and filtered to collect a solid. The solid was slurried in 500 mL of water for one hour and then was collected by filtration. The filter cake was washed with water and dried to yield 9.1 grams of ethyl (4-bromoethyl-3-chlorophenyl)carbamate; m.p. 112°–114° C.

Step C

Synthesis of 2-[[2-chloro-4-(ethoxycarbonylamino)phenyl]methyl]-4,4-dimethyl-3-isoxazolidinone as an intermediate Using a method analogous to that disclosed in Example 1, Step C, of U.S. Pat. No. 4,552,585, a suspension of 4.1 grams (0.030 mole) of potassium carbonate and 0.16 grams (0.02 equiv.) of 1,4,7,10,13,16-hexaoxacyclooctadecane in 100 mL of acetonitrile was stirred at ambient temperature, and a mixture of 3.4 grams (0.03 mole) of 4,4-dimethyl-3-isoxazolidinone and 8.6 grams (0.03 mole) of ethyl (4-bromomethyl-3-chlorophenyl)carbamate in 50 mL of acetonitrile was added dropwise. The complete addition required 30 minutes after which the reaction mixture was stirred for 40 hours. The reaction mixture was filtered to collect a solid. The solid was slurried in 500 mL of water for one hour and then was collected by filtration. The solid was dried to yield 7.7 grams of 2-[[2-chloro-4-ethoxycarbonylamino)phenyl]methyl]-4,4-dimethyl-3-isoxazolidinone; m.p. 162°–164° C.

The nmr spectrum was consistent with the proposed structure.

Step D

Synthesis of 2-[(4-amino-2-chlorophenyl)methyl]-4,4-dimethyl-3-isoxazolidinone

A mixture of 2.0 grams (0.006 mole) of 2-[[2-chloro-4-(ethoxycarbonylamino)phenyl]methyl]-4,4-dimethyl-3-isoxazolidinone in 20 mL of chloroform was stirred under an argon atmosphere, and 1.1 mL (0.007 mole) of iodotrimethylsilane was added via syringe. The reaction mixture was heated to 60° C. where it was stirred for two hours. After this time the reaction mixture was warmed to 70° C. where it was stirred for 16 hours. The reaction mixture was cooled to ambient temperature, and 10 mL of methanolic 2N hydrochloric acid was added. The resultant clear solution was concentrated under reduced pressure, and the residue was slurried in 50 mL of water. An insoluble material was removed by filtration, and the filtrate was neutralized with an aqueous solution saturated with sodium bicarbonate. The mixture was extracted with methylene chloride, and the combined extracts were dried with magnesium sulfate. The mixture was filtered, and the filtrate was concentrated under reduced pressure to a solid residue. The solid was recrystallized from hexane-ethyl acetate to yield 0.4 gram of 2-[(4-amino-2-chlorophenyl)methyl]-4,4-dimethyl-3-isoxazolidinone; m.p. 105°–107° C.

The nmr spectrum was consistent with the proposed structure.

EXAMPLE 2

SYNTHESIS OF 2-[(4-AMINO-2-CHLOROPHENYL)METHYL]-4,4-DIMETHYL-3-ISOXAZOLIDINONE HYDROCHLORIDE (Compound 3)

A solution of 2.0 grams (0.008 mole) of 2-[(4-amino-2-chlorophenyl)methyl]-4,4-dimethyl-3-isoxazolidinone in 25 mL of methanol was stirred, and 0.78 gram (0.008 mole) of concentrated hydrochloric acid was added dropwise. Upon completion of addition the reaction mixture was stirred for 20 minutes. Analysis of the reaction mixture by thin layer chromatography (TLC) indicated the presence of unreacted amine. An additional 0.5 gram of concentrated hydrochloric acid was added, and the reaction mixture was stirred for 30 minutes more. The reaction mixture was concentrated under reduced pressure to a residue. The residue was dissolved in 20 mL of ethanol. A solid was precipitated from the solution by the addition of 20 mL of diethyl ether. The solid was collected by filtration and was dried to yield 1.7 grams of 2-[(4-amino-2-chlorophenyl)methyl]-4,4-dimethyl-3-isoxazolidinone hydrochloride as a solid.

The nmr spectrum was consistent with the proposed structure.

The plant growth and development modifiers of the present invention were investigated for activity in preemergence and postemergence tests according to the following procedure:

Flats were filled with a steam sterilized sandy loam soil. Seeds of the following test plant species were planted in furrows: cotton (*Gossypium hirsutum*), lima bean (*Phaseolus limensis*), field corn (*Zea mays L.*), soybean (*Glycine max*), wheat (*Triticum aestivum*), barnyardgrass (*Echinochloa crus-galli*), johnsongrass (*Sorghum halepense*), pitted morningglory (*Ipomoea lacunosa*), velvetleaf (*Abutilon theophrasti*), field bindweed (*Convolvulus arvensis*), and green foxtail (*Setaria viridis*). Soil was leveled to a 1 cm depth over the seeds.

In both the preemergence and postemergence tests the test chemicals were applied as aqueous acetone solutions at a rate equivalent to 8.0 kilograms/hectare.

A flat for preemergence tests was watered and the soil evenly drenched with the water-acetone solution of test chemical. The treated flat was placed in a greenhouse where it was watered regularly at the soil surface for a period of 13 days. The effect of the test chemical was then recorded.

A flat for postemergence test was placed in a greenhouse for an 8 to 10 day growing period. The test solution was then hand-sprayed onto the foliage of the emerged test plants. After spraying, the foliage of the test plants was kept dry for 24 hours after which time regular watering was resumed for a period of 13 days. The effect of the test chemical was then recorded.

In the tests the plants were examined for herbicidal activity and morphological responses indicative of plant regulator activity. Virtually all compounds displayed some herbicidal activity at high application rates, i.e., rates of about 8 kg/ha.

Morphological responses that are indicative of plant regulator activity and that were observed when plants were treated with compounds of this invention include:

Stunting (Activity B) is manifested by treated plants which do not grow as tall as untreated plants. This plant regulator effect can be utilized with grasses in the maintenance of lawns, golf courses, and highway rights of way by reducing the frequency of mowings. Cereal and broadleaf crops such as wheat, cotton, and soybeans that have been treated with a chemical which causes stunting develop shorter, thicker stems which resist lodging, thus allowing more complete harvesting of the crop. Stem growth in treated fruit trees may be reduced, resulting in reduced need for pruning and a concomitant reduction in time expended in trimming the trees.

Axillary growth stimulation (Activity D) is manifested by increased branching, particularly in the angle between a leaf or branch and the axis from which it originates. In cereals such as wheat axillary growth stimulation leads to multiple stems known as tillers. In soybeans axillary stimulation at flowering can result in increased pod set. In both cereals and soybeans an increased yield may result from the treatment.

Nastic response (Activity E) is manifested by the twisting and bending of plants or parts thereof which is indicative of a hormonal change or disruption. A natural and useful nastic response is the curling of a tendril or a stem around a support, e.g., in peas or pole beans.

Intumescence (Activity J) is manifested by the formation of abnormal swellings and is indicative of a disruption of the hormonal balance required for normal growth. Intumescence-causing agents can promote growth of tissue, such as tobacco callus.

Negative root geotropism (Activity M) is the upward growth of roots out of the soil and is indicative of a disruption of the plant's normal hormonal balance. This effect can be correlated with an increase in the number of pods on treated soybean plants.

Deeper green lower leaves (Activity P) suggests delay of senescence, increased chlorophyll production, or chlorophyll retention.

The responses indicating plant regulatory activity in preemergence and postemergence applications are set forth in Table II.

TABLE II

| Cmpd. No. | Test Type[1] | Plant Growth Regulating Morphological Response[2] | | | | |
|---|---|---|---|---|---|---|
| | | Lima Bean | Soybean | Cotton | Corn | Wheat |
| 1 | PRE | B | BD | * | — | — |
| | POST | B | BD | * | — | — |
| 2 | PRE | BJ | B | * | B | — |
| | POST | BE | BE | * | — | — |
| 3 | PRE | B | BJE | * | B | — |
| | POST | BDE | BDE | * | — | M |
| 4 | PRE | * | B | — | — | — |
| | POST | * | BDE | — | B | — |
| 5 | PRE | B | B | * | — | — |
| | POST | B | BD | * | — | — |
| 6 | PRE | * | B | — | B | — |
| | POST | * | BDE | — | B | — |
| 7 | PRE | * | B | — | — | — |
| | POST | * | B | — | — | — |
| 8 | PRE | * | B | — | P | B |
| | POST | * | BD | — | — | — |
| 9 | PRE | * | B | B | B | B |
| | POST | * | B | — | — | — |

*Not tested
— Did not show plant growth regulating morphological response.
[1]PRE = Preemergence, POST = Postemergence
[2]B = Stunting
D = Axillary growth stimulation
E = Nastic responses
J = Intumescence
M = Negative root geotropism
P = Darker green basal leaves

What is claimed is:

1. A method for beneficially modifying growth and development of plants for producing agricultural crops which comprises applying to the plant or to the site where the plant is or is about to be planted a substantially non-toxic plant regulating amount of a 2-[(4-aminophenyl)methyl]-4,4-dimethyl-3-isoxazolidinone of the formula

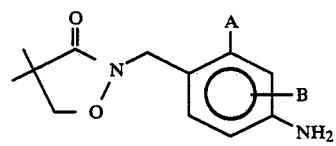

or an agriculturally acceptable salt thereof in which A is hydrogen or halogen, B is hydrogen or halogen, or A and B together form —$C_4H_4$— bridging adjacent carbon atoms.

* * * * *